(12) United States Patent
Aranyi et al.

(10) Patent No.: US 8,900,253 B2
(45) Date of Patent: Dec. 2, 2014

(54) CLIP APPLYING APPARATUS WITH ANGLED JAW

(75) Inventors: Ernest Aranyi, Easton, CT (US);
Kenneth H. Whitfield, New Haven, CT (US)

(73) Assignee: Covidien LP, Mansfield, MA (US)

( * ) Notice: Subject to any disclaimer, the term of this patent is extended or adjusted under 35 U.S.C. 154(b) by 1873 days.

(21) Appl. No.: 10/547,902

(22) PCT Filed: Mar. 11, 2004

(86) PCT No.: PCT/US2004/007401
§ 371 (c)(1),
(2), (4) Date: Sep. 7, 2005

(87) PCT Pub. No.: WO2004/080290
PCT Pub. Date: Sep. 23, 2004

(65) Prior Publication Data
US 2006/0184182 A1 Aug. 17, 2006

Related U.S. Application Data

(60) Provisional application No. 60/453,581, filed on Mar. 11, 2003.

(51) Int. Cl.
*A61B 17/10* (2006.01)
(Continued)

(52) U.S. Cl.
CPC ..... *A61B 17/122* (2013.01); *A61B 2018/00702* (2013.01); *A61B 2018/00875* (2013.01);
(Continued)

(58) Field of Classification Search
CPC ............. A61B 17/122; A61B 17/1285; A61B 2017/2926; A61B 17/0682; A61B 17/068; A61B 2017/00584; A61B 17/10; A61B 17/128; A61B 17/0487; A61B 2017/0488; A61B 17/08; A61B 17/083; A61B 17/22; A61B 17/12; A61B 17/282; A61B 17/2944
USPC .......................... 606/207, 142, 139, 143, 219; 227/175.1, 181.1; 72/409.02
See application file for complete search history.

(56) References Cited

U.S. PATENT DOCUMENTS 3,120,230 A 2/1964 Skold
3,270,745 A * 9/1966 Wood ............................ 606/158
(Continued)

FOREIGN PATENT DOCUMENTS

WO WO 9747245 A1 * 12/1997

OTHER PUBLICATIONS

International Search Report for International Appln No. PCT/US04/07401, Mar. 11, 2004

*Primary Examiner* — Darwin Erezo
*Assistant Examiner* — Erin Colello (57) ABSTRACT

A clip applying apparatus is provided which includes a jaw mechanism having a stationary jaw and a movable jaw. The movable jaw is supported on or formed integrally with the distal end of a crimping member which is movably supported within a body portion of the apparatus. The stationary jaw defines a longitudinal axis which forms an angle θ of between about 15 degrees and about 15 degrees and about 75 degrees in relation to a longitudinal axis of the body portion. In another embodiment, the stationary jaw includes a clip receiving channel which is configured to at least partially receive a surgical clip. In one embodiment, the distal end of the stationary jaw includes a stop member which is positioned to engage the distal end of the stationary jaw includes a stop member which is positioned to engage the distal end of a leg of a surgical clip to prevent the surgical clip from being pushed from the stationary jaw during operation of the apparatus and the movable jaw includes a distally located crimping surface and a head portion defining a recessed channel configured to receive a portion of a surgical clip supported on the stationary jaw. In yet another embodiment, the crimping surface defines an acute angle β in relation to the longitudinal axis of the body portion, and in one embodiment, angle β is substantially the same as angle θ.

20 Claims, 5 Drawing Sheets

(51) Int. Cl.
*A61B 17/128* (2006.01)
*A61B 17/122* (2006.01)
*A61B 18/14* (2006.01)
*A61B 18/00* (2006.01)
*A61B 17/29* (2006.01)

(52) U.S. Cl.
CPC ... *A61B 17/1285* (2013.01); *A61B 2018/00791* (2013.01); *A61B 2017/2926* (2013.01); *A61B 2018/0063* (2013.01); *A61B 18/1445* (2013.01)
USPC .................................................... 606/142

(56) References Cited

U.S. PATENT DOCUMENTS

| | | | | |
|---|---|---|---|---|
| 3,463,156 | A * | 8/1969 | McDermott et al. | 606/158 |
| 3,601,302 | A * | 8/1971 | Potekhina et al. | 227/120 |
| 3,638,847 | A | 2/1972 | Noiles et al. | |
| 3,665,924 | A * | 5/1972 | Noiles et al. | 606/143 |
| 3,777,538 | A * | 12/1973 | Weatherly et al. | 72/409.01 |
| 3,828,791 | A * | 8/1974 | Santos | 606/207 |
| 3,882,854 | A * | 5/1975 | Hulka et al. | 600/104 |
| 4,064,881 | A * | 12/1977 | Meredith | 606/142 |
| 4,169,476 | A * | 10/1979 | Hiltebrandt | 606/142 |
| 4,296,751 | A | 10/1981 | Blake, III et al. | |
| 4,325,377 | A * | 4/1982 | Boebel | 606/142 |
| 4,372,316 | A | 2/1983 | Blake, III et al. | |
| 4,408,603 | A | 10/1983 | Blake, III et al. | |
| 4,427,008 | A * | 1/1984 | Transue | 606/143 |
| 4,440,170 | A * | 4/1984 | Golden et al. | 606/142 |
| 4,450,840 | A * | 5/1984 | Mericle et al. | 606/143 |
| 4,480,640 | A | 11/1984 | Becht | |
| 4,480,641 | A | 11/1984 | Failla et al. | |
| 4,487,204 | A | 12/1984 | Hrouda | |
| 4,487,205 | A | 12/1984 | Di Giovanni et al. | |
| 4,491,133 | A | 1/1985 | Menges et al. | |
| 4,492,232 | A | 1/1985 | Green | |
| 4,498,476 | A | 2/1985 | Cerwin et al. | |
| 4,500,024 | A | 2/1985 | DiGiovanni et al. | |
| 4,509,518 | A | 4/1985 | McGarry et al. | |
| 4,512,345 | A | 4/1985 | Green | |
| 4,522,207 | A | 6/1985 | Klieman et al. | |
| 4,532,925 | A | 8/1985 | Blake, III | |
| 4,534,351 | A | 8/1985 | Rothfuss et al. | |
| 4,545,377 | A | 10/1985 | Cerwin et al. | |
| 4,549,544 | A | 10/1985 | Favaron | |
| 4,556,058 | A * | 12/1985 | Green | 606/143 |
| 4,557,263 | A | 12/1985 | Green | |
| 4,562,839 | A | 1/1986 | Blake, III et al. | |
| 4,572,183 | A | 2/1986 | Juska | |
| 4,576,165 | A | 3/1986 | Green et al. | |
| 4,576,166 | A | 3/1986 | Montgomery et al. | |
| 4,579,118 | A * | 4/1986 | Failla | 606/158 |
| 4,590,937 | A | 5/1986 | Deniega | |
| 4,598,711 | A | 7/1986 | Deniega | |
| 4,602,631 | A | 7/1986 | Funatsu | |
| 4,611,595 | A | 9/1986 | Klieman et al. | |
| 4,612,932 | A | 9/1986 | Caspar et al. | |
| 4,616,650 | A * | 10/1986 | Green et al. | 606/143 |
| 4,616,651 | A | 10/1986 | Golden | |
| 4,624,254 | A * | 11/1986 | McGarry et al. | 606/143 |
| 4,637,395 | A | 1/1987 | Caspar et al. | |
| 4,646,740 | A | 3/1987 | Peters et al. | |
| 4,647,504 | A | 3/1987 | Kimimura et al. | |
| 4,651,737 | A * | 3/1987 | Deniega | 606/158 |
| 4,658,822 | A | 4/1987 | Kees, Jr. | |
| 4,660,558 | A | 4/1987 | Kees, Jr. | |
| 4,662,373 | A | 5/1987 | Montgomery et al. | |
| 4,662,374 | A | 5/1987 | Blake, III | |
| 4,671,278 | A | 6/1987 | Chin | |
| 4,671,282 | A | 6/1987 | Tretbar | |
| 4,674,504 | A | 6/1987 | Klieman et al. | |
| 4,681,107 | A | 7/1987 | Kees, Jr. | |
| 4,696,396 | A | 9/1987 | Samuels | |
| 4,702,247 | A | 10/1987 | Blake, III et al. | |
| 4,706,668 | A | 11/1987 | Backer | |
| 4,712,549 | A | 12/1987 | Peters et al. | |
| 4,733,664 | A | 3/1988 | Kirsch et al. | |
| 4,733,666 | A | 3/1988 | Mercer, Jr. | |
| 4,759,364 | A | 7/1988 | Boebel | |
| 4,765,335 | A | 8/1988 | Schmidt et al. | |
| 4,777,949 | A | 10/1988 | Perlin | |
| 4,777,950 | A | 10/1988 | Kees, Jr. | |
| 4,796,625 | A | 1/1989 | Kees, Jr. | |
| 4,799,481 | A | 1/1989 | Transue et al. | |
| 4,815,466 | A | 3/1989 | Perlin | |
| 4,817,604 | A | 4/1989 | Smith, III | |
| 4,821,721 | A | 4/1989 | Chin et al. | |
| 4,822,348 | A | 4/1989 | Casey | |
| 4,827,930 | A | 5/1989 | Kees, Jr. | |
| 4,834,096 | A | 5/1989 | Oh et al. | |
| 4,850,355 | A | 7/1989 | Brooks et al. | |
| 4,854,317 | A | 8/1989 | Braun | |
| 4,856,517 | A | 8/1989 | Collins et al. | |
| 4,877,028 | A * | 10/1989 | Sandhaus | 606/158 |
| 4,929,239 | A | 5/1990 | Braun | |
| 4,929,240 | A | 5/1990 | Kirsch et al. | |
| 4,931,058 | A | 6/1990 | Cooper | |
| 4,932,955 | A | 6/1990 | Merz et al. | |
| 4,934,364 | A | 6/1990 | Green | |
| 4,943,298 | A | 7/1990 | Fujita et al. | |
| 4,957,500 | A | 9/1990 | Liang et al. | |
| 4,966,603 | A | 10/1990 | Focelle et al. | |
| 4,967,949 | A * | 11/1990 | Sandhaus | 227/176.1 |
| 4,983,176 | A | 1/1991 | Cushman et al. | |
| 4,988,355 | A | 1/1991 | Leveen et al. | |
| 5,002,552 | A | 3/1991 | Casey | |
| 5,026,379 | A | 6/1991 | Yoon | |
| 5,030,224 | A | 7/1991 | Wright et al. | |
| 5,030,226 | A | 7/1991 | Green et al. | |
| 5,032,127 | A | 7/1991 | Frazee et al. | |
| 5,035,692 | A | 7/1991 | Lyon et al. | |
| 5,047,038 | A | 9/1991 | Peters et al. | |
| 5,049,152 | A | 9/1991 | Simon et al. | |
| 5,049,153 | A | 9/1991 | Nakao et al. | |
| 5,053,045 | A | 10/1991 | Schmidt et al. | |
| 5,059,202 | A | 10/1991 | Liang et al. | |
| 5,062,846 | A * | 11/1991 | Oh et al. | 606/158 |
| 5,078,731 | A | 1/1992 | Hayhurst | |
| 5,084,057 | A | 1/1992 | Green et al. | |
| 5,100,416 | A | 3/1992 | Oh et al. | |
| 5,100,420 | A | 3/1992 | Green et al. | |
| 5,104,394 | A | 4/1992 | Knoepfler | |
| 5,104,395 | A | 4/1992 | Thornton et al. | |
| 5,112,343 | A | 5/1992 | Thornton | |
| 5,122,150 | A | 6/1992 | Puig | |
| 5,127,915 | A | 7/1992 | Mattson | |
| 5,129,885 | A | 7/1992 | Green et al. | |
| 5,156,608 | A | 10/1992 | Troidl et al. | |
| 5,160,339 | A | 11/1992 | Chen et al. | |
| 5,163,945 | A | 11/1992 | Ortiz et al. | |
| 5,171,247 | A * | 12/1992 | Hughett et al. | 606/142 |
| 5,171,249 | A | 12/1992 | Stefanchik et al. | |
| 5,171,250 | A | 12/1992 | Yoon | |
| 5,171,251 | A | 12/1992 | Bregen et al. | |
| 5,171,252 | A | 12/1992 | Friedland | |
| 5,171,253 | A | 12/1992 | Klieman | |
| 5,176,695 | A * | 1/1993 | Dulebohn | 606/170 |
| 5,192,288 | A | 3/1993 | Thompson et al. | |
| 5,197,970 | A | 3/1993 | Green et al. | |
| 5,199,566 | A | 4/1993 | Ortiz et al. | |
| 5,201,746 | A | 4/1993 | Shichman | |
| 5,201,900 | A | 4/1993 | Nardella | |
| 5,207,691 | A | 5/1993 | Nardella | |
| 5,207,692 | A | 5/1993 | Kraus et al. | |
| 5,217,473 | A | 6/1993 | Yoon | |
| 5,219,353 | A * | 6/1993 | Garvey et al. | 606/157 |
| 5,246,450 | A | 9/1993 | Thornton et al. | |
| 5,269,792 | A | 12/1993 | Kovac et al. | |
| 5,281,228 | A | 1/1994 | Wolfson | |
| 5,282,807 | A | 2/1994 | Knoepfler | |
| 5,282,808 | A * | 2/1994 | Kovac et al. | 606/143 |
| 5,282,832 | A | 2/1994 | Toso et al. | |
| 5,290,299 | A | 3/1994 | Fain et al. | |

(56) References Cited

U.S. PATENT DOCUMENTS

| | | | |
|---|---|---|---|
| 5,300,081 A | 4/1994 | Young et al. | |
| 5,304,183 A | 4/1994 | Gourlay et al. | |
| 5,306,280 A | 4/1994 | Bregen et al. | |
| 5,306,283 A | 4/1994 | Conners | |
| 5,312,426 A | 5/1994 | Segawa et al. | |
| 5,330,442 A | 7/1994 | Green et al. | |
| 5,330,487 A | 7/1994 | Thornton et al. | |
| 5,336,229 A * | 8/1994 | Noda | 606/144 |
| 5,340,360 A * | 8/1994 | Stefanchik | 606/142 |
| 5,342,373 A | 8/1994 | Stefanchik et al. | |
| 5,354,304 A | 10/1994 | Allen et al. | |
| 5,354,306 A * | 10/1994 | Garvey et al. | 606/157 |
| 5,366,134 A * | 11/1994 | Green et al. | 227/176.1 |
| 5,366,458 A | 11/1994 | Korthoff et al. | |
| 5,366,459 A | 11/1994 | Yoon | |
| 5,368,600 A | 11/1994 | Failla et al. | |
| 5,382,253 A | 1/1995 | Hogendijk | |
| 5,382,254 A | 1/1995 | McGarry et al. | |
| 5,382,255 A | 1/1995 | Castro et al. | |
| 5,383,881 A | 1/1995 | Green et al. | |
| 5,395,381 A | 3/1995 | Green et al. | |
| 5,403,327 A | 4/1995 | Thornton et al. | |
| 5,409,498 A | 4/1995 | Braddock et al. | |
| 5,413,584 A | 5/1995 | Schulze | |
| 5,423,835 A | 6/1995 | Green et al. | |
| 5,425,740 A | 6/1995 | Hutchinson, Jr. | |
| 5,431,667 A | 7/1995 | Thompson et al. | |
| 5,431,668 A * | 7/1995 | Burbank et al. | 606/143 |
| 5,431,669 A | 7/1995 | Thompson et al. | |
| 5,439,468 A | 8/1995 | Schulze et al. | |
| 5,441,509 A | 8/1995 | Vidal et al. | |
| 5,447,513 A | 9/1995 | Davison et al. | |
| 5,449,365 A * | 9/1995 | Green et al. | 606/142 |
| 5,462,555 A | 10/1995 | Bolanos et al. | |
| 5,462,558 A | 10/1995 | Kolesa et al. | |
| 5,464,416 A | 11/1995 | Steckel | |
| 5,474,566 A | 12/1995 | Alesi et al. | |
| 5,474,567 A | 12/1995 | Stefanchik et al. | |
| 5,474,572 A | 12/1995 | Hayhurst | |
| 5,487,746 A | 1/1996 | Yu et al. | |
| 5,501,693 A | 3/1996 | Gravener | |
| 5,509,920 A | 4/1996 | Phillips et al. | |
| 5,514,149 A | 5/1996 | Green et al. | |
| 5,520,701 A | 5/1996 | Lerch | |
| 5,522,823 A | 6/1996 | Kuntz et al. | |
| 5,527,318 A | 6/1996 | McGarry | |
| 5,527,319 A | 6/1996 | Green et al. | |
| 5,527,320 A | 6/1996 | Carruthers et al. | |
| 5,542,949 A | 8/1996 | Yoon | |
| 5,547,474 A * | 8/1996 | Kloeckl et al. | 606/143 |
| 5,569,274 A | 10/1996 | Rapacki et al. | |
| 5,571,121 A | 11/1996 | Heifetz | |
| 5,575,802 A | 11/1996 | McQuildin et al. | |
| 5,582,615 A | 12/1996 | Foshee et al. | |
| 5,584,840 A | 12/1996 | Ramsey et al. | |
| 5,591,178 A | 1/1997 | Green et al. | |
| 5,593,414 A | 1/1997 | Shipp et al. | |
| 5,593,421 A | 1/1997 | Bauer | |
| 5,601,573 A | 2/1997 | Fogelberg et al. | |
| 5,601,574 A | 2/1997 | Stefanchik et al. | |
| 5,607,436 A | 3/1997 | Pratt et al. | |
| 5,618,291 A * | 4/1997 | Thompson et al. | 606/142 |
| 5,618,306 A * | 4/1997 | Roth et al. | 606/205 |
| 5,620,452 A | 4/1997 | Yoon | |
| 5,626,585 A | 5/1997 | Mittelstadt et al. | |
| 5,626,586 A | 5/1997 | Pistl et al. | |
| 5,626,592 A | 5/1997 | Phillips et al. | |
| RE35,525 E | 6/1997 | Stefanchik et al. | |
| 5,634,930 A | 6/1997 | Thornton et al. | |
| 5,643,291 A | 7/1997 | Pier et al. | |
| 5,645,551 A | 7/1997 | Green et al. | |
| 5,645,553 A | 7/1997 | Kolesa et al. | |
| 5,649,937 A | 7/1997 | Bito et al. | |
| 5,653,720 A | 8/1997 | Johnson et al. | |
| 5,662,676 A | 9/1997 | Koninckx | |
| 5,662,679 A | 9/1997 | Voss et al. | |
| 5,664,662 A | 9/1997 | Witt et al. | |
| 5,665,097 A * | 9/1997 | Baker et al. | 606/143 |
| 5,676,676 A | 10/1997 | Porter | |
| 5,681,330 A | 10/1997 | Hughett et al. | |
| 5,683,405 A | 11/1997 | Yacoubian et al. | |
| 5,695,502 A | 12/1997 | Pier et al. | |
| 5,695,505 A | 12/1997 | Yoon | |
| 5,697,938 A | 12/1997 | Jensen et al. | |
| 5,700,270 A | 12/1997 | Peyser et al. | |
| 5,700,271 A | 12/1997 | Whitfield et al. | |
| 5,702,048 A | 12/1997 | Eberlin | |
| 5,709,706 A | 1/1998 | Kienzle et al. | |
| 5,713,911 A | 2/1998 | Racenet et al. | |
| 5,713,912 A | 2/1998 | Porter | |
| 5,720,756 A | 2/1998 | Green et al. | |
| 5,722,982 A | 3/1998 | Ferreira et al. | |
| 5,725,537 A | 3/1998 | Green et al. | |
| 5,725,538 A | 3/1998 | Green et al. | |
| 5,725,542 A | 3/1998 | Yoon | |
| 5,733,295 A | 3/1998 | Back et al. | |
| 5,755,726 A | 5/1998 | Pratt et al. | |
| 5,766,189 A | 6/1998 | Matsuno | |
| 5,766,205 A * | 6/1998 | Zvenyatsky et al. | 606/206 |
| 5,769,857 A | 6/1998 | Reztzov et al. | |
| 5,772,673 A * | 6/1998 | Cuny et al. | 606/142 |
| 5,776,146 A | 7/1998 | Sackier et al. | |
| 5,776,147 A | 7/1998 | Dolendo | |
| 5,779,718 A | 7/1998 | Green et al. | |
| 5,779,720 A | 7/1998 | Walder-Utz et al. | |
| 5,782,844 A | 7/1998 | Yoon et al. | |
| 5,788,698 A | 8/1998 | Savornin | |
| 5,792,149 A | 8/1998 | Sherts et al. | |
| 5,792,150 A | 8/1998 | Pratt et al. | |
| 5,797,922 A | 8/1998 | Hessel et al. | |
| 5,810,853 A | 9/1998 | Yoon | |
| 5,810,877 A * | 9/1998 | Roth et al. | 606/205 |
| 5,817,116 A | 10/1998 | Takahashi et al. | |
| 5,824,547 A | 10/1998 | Hashino et al. | |
| 5,824,548 A | 10/1998 | Hearn | |
| 5,827,306 A | 10/1998 | Yoon | |
| 5,833,695 A | 11/1998 | Yoon | |
| 5,833,696 A * | 11/1998 | Whitfield et al. | 606/143 |
| 5,833,700 A | 11/1998 | Fogelberg et al. | |
| 5,835,199 A | 11/1998 | Phillips et al. | |
| 5,843,097 A | 12/1998 | Mayenberger et al. | |
| 5,843,101 A | 12/1998 | Fry | |
| 5,846,255 A | 12/1998 | Casey | |
| 5,849,019 A | 12/1998 | Yoon | |
| 5,858,018 A | 1/1999 | Shipp et al. | |
| 5,861,018 A | 1/1999 | Feierbach | |
| 5,868,759 A | 2/1999 | Peyser et al. | |
| 5,868,761 A * | 2/1999 | Nicholas et al. | 606/143 |
| 5,876,410 A | 3/1999 | Petillo | |
| 5,895,394 A | 4/1999 | Kienzle et al. | |
| 5,897,565 A | 4/1999 | Foster | |
| 5,904,693 A | 5/1999 | Diesare et al. | |
| 5,906,625 A * | 5/1999 | Bito et al. | 606/142 |
| 5,913,862 A | 6/1999 | Ramsey et al. | |
| 5,921,996 A | 7/1999 | Sherman | |
| 5,928,251 A | 7/1999 | Aranyi et al. | |
| 5,938,667 A * | 8/1999 | Peyser et al. | 606/142 |
| 5,951,574 A | 9/1999 | Stefanchik et al. | |
| 5,972,003 A | 10/1999 | Rousseau et al. | |
| 5,976,159 A | 11/1999 | Bolduc et al. | |
| 5,993,465 A * | 11/1999 | Shipp et al. | 606/142 |
| 6,004,335 A | 12/1999 | Vaitekunas et al. | |
| 6,017,358 A | 1/2000 | Yoon et al. | |
| RE36,720 E * | 5/2000 | Green et al. | 606/151 |
| 6,059,799 A * | 5/2000 | Aranyi et al. | 606/143 |
| 6,099,536 A | 8/2000 | Petillo | |
| 6,099,537 A * | 8/2000 | Sugai et al. | 606/143 |
| 6,139,555 A * | 10/2000 | Hart et al. | 606/139 |
| 6,210,418 B1 | 4/2001 | Storz et al. | |
| 6,217,590 B1 | 4/2001 | Levinson | |
| 6,228,097 B1 | 5/2001 | Levinson et al. | |
| 6,241,740 B1 | 6/2001 | Davis et al. | |
| 6,258,105 B1 | 7/2001 | Hart et al. | |
| 6,261,302 B1 | 7/2001 | Voegele et al. | |

(56) References Cited

U.S. PATENT DOCUMENTS

| | | | |
|---|---|---|---|
| 6,273,898 B1 | 8/2001 | Kienzle et al. |
| 6,277,131 B1 | 8/2001 | Kailow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 * | 12/2002 | Wilk et al. ............... 606/142 |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forseter et al. |
| 6,602,252 B2 | 8/2003 | Mollenauer |
| 6,607,540 B1 * | 8/2003 | Shipp ............... 606/143 |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,793,666 B2 | 9/2004 | Kenifel et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Mantakis et al. |
| 6,843,794 B2 | 1/2005 | Sixto et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | DeGuillebon et al. |
| 6,913,607 B2 | 7/2005 | Ainsworth et al. |
| 6,916,327 B2 | 7/2005 | Northrup et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto et al. |
| 6,966,981 B2 | 11/2005 | Binder et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,446 B2 | 12/2005 | Hommann et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,597 B2 | 1/2006 | Gellman et al. |
| 6,991,634 B2 | 1/2006 | Sugiyama et al. |
| 6,991,635 B2 | 1/2006 | Takamoto et al. |
| 7,052,504 B2 | 5/2006 | Hughett |
| 7,056,330 B2 | 6/2006 | Gayton |
| 7,343,920 B2 * | 3/2008 | Toby et al. ............... 128/898 |
| 7,635,385 B2 * | 12/2009 | Milliman et al. ............... 623/1.23 |
| 7,637,917 B2 * | 12/2009 | Whitfield et al. ............... 606/143 |
| 2001/0047178 A1 * | 11/2001 | Peters ............... 606/139 |
| 2002/0068947 A1 | 6/2002 | Kuhns et al. |
| 2002/0082085 A1 | 6/2002 | Shipp et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |

(56) References Cited

U.S. PATENT DOCUMENTS

| | | |
|---|---|---|
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Franceses et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0111731 A1 | 5/2006 | Manzo |
| 2006/0184182 A1 | 8/2006 | Aranyi et al. |
| 2006/0190013 A1 | 8/2006 | Menn |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |

\* cited by examiner

CLIP APPLYING APPARATUS WITH ANGLED JAW

CROSS REFERENCE TO RELATED APPLICATIONS

This application claims the benefit of and priority to International Application Serial No. PCT/US2004/007401 filed Mar. 11, 2004, which, in turn, claims the benefit of and priority to U.S. Provisional Application Ser. No. 60/453,581 filed on Mar. 11, 2003, entitled "CLIP APPLYING APPARATUS WITH ANGLED JAW", and incorporates its entire contents by reference herein.

BACKGROUND

1. Technical Field

The present disclosure relates to clip applying apparatus and ligation clips. More particularly, the present disclosure relates to clip applying apparatus for applying surgical clips to body tissue during surgical procedures which provide enhanced visibility at the surgical site.

2. Background to Related Art

Surgical procedures frequently require ligation of blood vessels, severed tissues and/or other organs to control or stop bleeding. Clip applying apparatus for quickly applying a surgical clip about tissue are well known. Such clip applying apparatus include single clip applicators and multiple clip applicators. In single clip applicators, a new clip must be loaded into the apparatus after application of each clip. Multiple clip applicators include a series of clips which can be sequentially applied to tissue during the course of a surgical procedure.

Typically, clip applying apparatus include a handle mechanism, an elongated body portion, and a clip crimping assembly, e.g., a jaw or pair of jaws. Such clip applying apparatus are configured for endoscopic or open surgical procedures. One problem associated with known clip applying apparatus is obstructed visualization of the surgical site especially during endoscopic surgical procedures. More specifically, the jaw structure and/or the distal end of the body portion obstructs the surgeon's view of the surgical site. Accordingly, a continuing need exists for a clip applying apparatus which provides improved visibility of the surgical site during application of a surgical clip to tissue.

SUMMARY

A clip applying apparatus is provided which includes a handle assembly, a body portion extending distally from the handle assembly and a jaw mechanism. The jaw mechanism includes a stationary jaw and a movable jaw. The movable jaw is supported on or formed integrally with the distal end of a crimping member which is movably supported within the body portion. The stationary jaw defines a longitudinal axis which forms an angle $\theta$ of between about 15 degrees and about 75 degrees in relation to a longitudinal axis of the body portion. In one embodiment, angle $\theta$ is about 25 degrees. In another embodiment, the stationary jaw includes a clip receiving channel which is configured to at least partially receive a surgical clip. In one embodiment, the distal end of the stationary jaw includes a stop member which is positioned to engage the distal end of a leg of a surgical clip to prevent the surgical clip from being pushed from the stationary jaw during operation of the apparatus.

In another embodiment, the movable jaw includes a distally located crimping surface and a head portion defining a recessed channel configured to receive a portion of a surgical clip supported on the stationary jaw. In yet another embodiment, crimping surface defines an acute angle $\beta$ in relation to the longitudinal axis of the body portion, and in one embodiment, angle $\beta$ is substantially equal to angle $\theta$. Because of the angles of the stationary jaw and the crimping surface of the movable jaw, the distal ends of the legs of a surgical clip are approximated before approximation of the proximal ends of the legs. By approximating the legs of the surgical clip in this manner, tissue positioned between the legs of the surgical clip is retained between the legs of the clip during clip formation.

BRIEF DESCRIPTION OF THE DRAWINGS

Various preferred embodiments of the presently disclosed clip applying apparatus are described herein with reference to the drawings.

DETAILED DESCRIPTION OF PREFERRED EMBODIMENTS

Preferred embodiments of the presently disclosed clip applying apparatus will now be described in detail with reference to the drawings, in which like reference numerals designate identical or corresponding elements in each of the several views.

Figure 1:
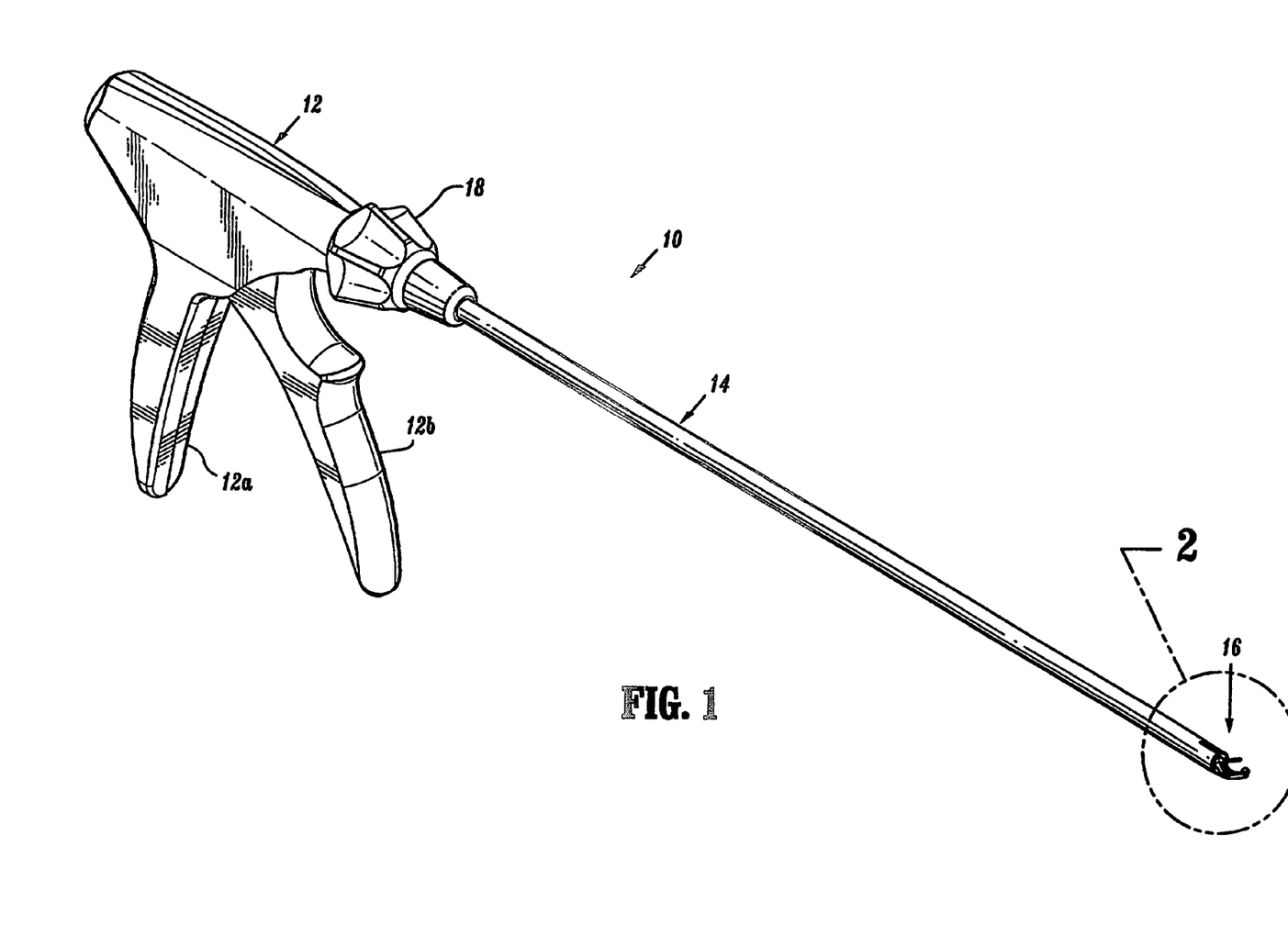
FIG. 1 is a side perspective view of one preferred embodiment of the presently disclosed clip applying apparatus.
Figure 2:
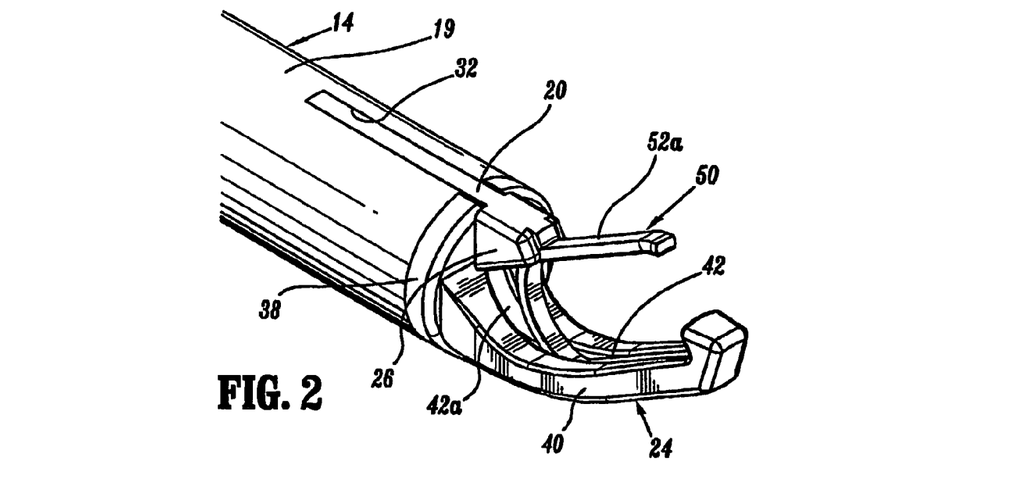
FIG. 2 is an enlarged view of the angled anvil jaw shown in the indicated area of detail of FIG. 1.

FIG. 1 illustrates one embodiment of the presently disclosed clip applying apparatus 10. Briefly, clip applying apparatus 10 includes a handle assembly 12 including a stationary handle 12a and a pivotable actuator trigger 12b, a central body portion 14 and a jaw mechanism 16. Although handle assembly 12 is illustrated having a pistol grip configuration other known handle configurations are envisioned, e.g., in-line handle, scissors handle, tweezers handle, etc. A rotatable knob 18 is rotatably supported on a distal end of handle assembly 12. Rotatable knob 18 supports the proximal end of central body portion 14 in a known manner such that rotatable knob 18, central body portion 14 and jaw mechanism 16 are rotatable in relation to handle assembly 12 about the longitudinal axis of central body portion 14. It is envisioned that the rotatable knob 18 can be configured to rotate the jaw mechanism 16 while the central body portion 14 remains stationary. Although specific details of the handle assembly 12 are not disclosed herein, the handle assembly 12 may include any handle mechanism known in the art to effect actuation of a clip pusher mechanism as will be described in detail below. Examples of such known handle mechanisms are well known and disclosed in U.S. Pat. Nos. 5,938,667, 5,868,761, 5,868,759, 5,725,538, 5,720,756, 5,700,270, 5,695,502, 5,645,553, 5,626,585, 5,591,178, 5,514,149, 5,462,558, 5,300,081, 5,197,970 and 4,509,518 all of which patents are incorporated herein in their entirety by reference.

Figure 9:
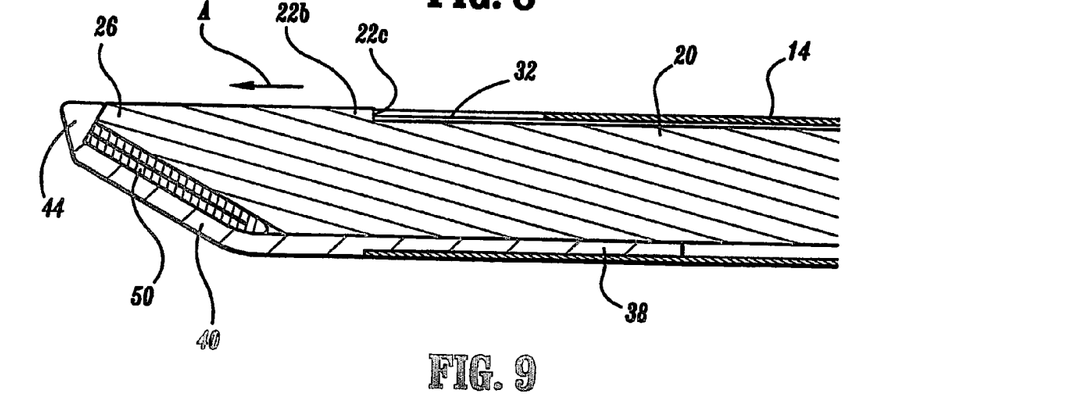
FIG. 9 is a side cross-sectional view of the distal end of the clip applying apparatus shown in FIG. 1 with a clip positioned in the anvil jaw about a vessel (not shown) and the crimping member in a fully advanced position.

Referring to FIGS. 2-5, jaw mechanism 16 includes a stationary jaw or anvil 24 and a movable jaw. The movable jaw is formed on a distal end 22 of a crimping member or pusher 20 and is movable from a proximal-most position (FIG. 7) to a distal-most position (FIG. 9). These components will be described in further detail below.

Central body portion 14 includes an outer housing 19 positioned about the internal components of central body portion 14 and a crimping member or pusher 20. Crimping member 20 includes a proximal end (not shown) which is operatively connected to handle assembly 12, in a known manner, such that actuation of pivotable trigger 12b effects substantially linear movement of crimping member 20 along a longitudinal axis of central body portion 14 from an initial or retracted position (FIG. 7) to one or more advanced positions (FIGS. 8 and 9), where one of the advanced positions is a final position (FIG. 9). The distal end 22 of crimping member 20 includes an angled crimping surface 22a including as guide slot or channel 28 positioned to receive, engage and crimp a surgical clip 50 supported on anvil 24 upon advancement of crimping member 20. Angled crimping surface 22a preferably defines an acute angle β of between about 15 degrees and about 75 degrees and more preferably between about 20 degrees and about 45 degrees in relation to the longitudinal axis "X" of central body portion 14. Most preferably, angled crimping surface 22a defines an angle of about 30 degrees. The distal end 22 of crimping member 20 also includes a head portion 26. Head portion 26 defines channel 28 at a position adjacent a distal portion of crimping surface 22a. Channel 28 (FIG. 3) is dimensioned to receive and retain a surgical clip 50 positioned in the anvil 24 between the anvil 24 and crimping surface 22a.

Crimping member 20 is slidably positioned within central body portion 14. The distal end 22 of crimping member 20 includes a raised surface 22b which with a proximal portion of crimping member 20 defines a shoulder or stop 22c. Raised surface 22b is configured to be slidably received within an elongated slot 32 formed in a distal end of central body portion 14. Stop 22c engages a stepped surface (not shown) of central body portion 14 to limit proximal movement of crimping member 20. Head portion 26 has a width greater than the width of slot 32 to define a pair of abutment surfaces 34 which engage a distal face 36 of anvil body 38 when crimping member 20 is in a retracted position to further limit proximal movement of crimping member 20.

Figure 3:
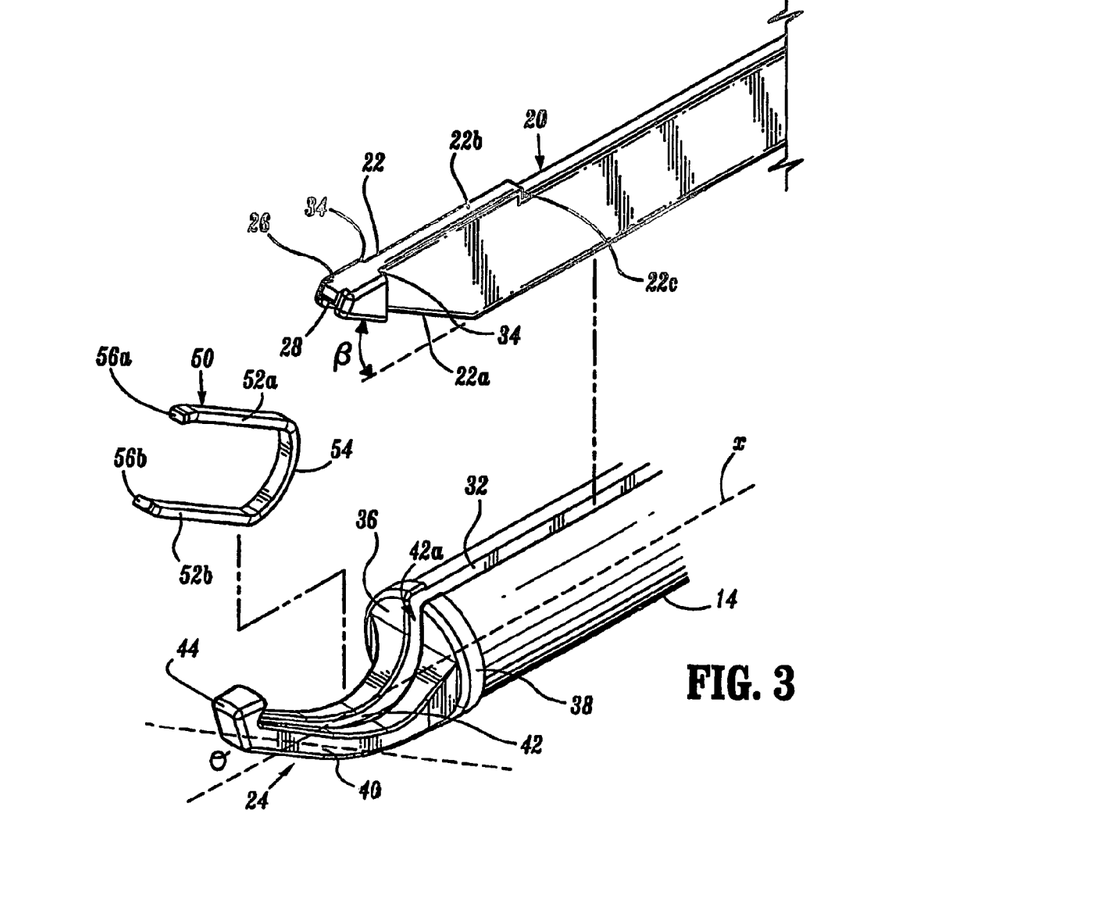
FIG. 3 is a side perspective view from the front of the distal end of the clip applying apparatus shown in FIG. 2 with parts separated.
Figure 4:
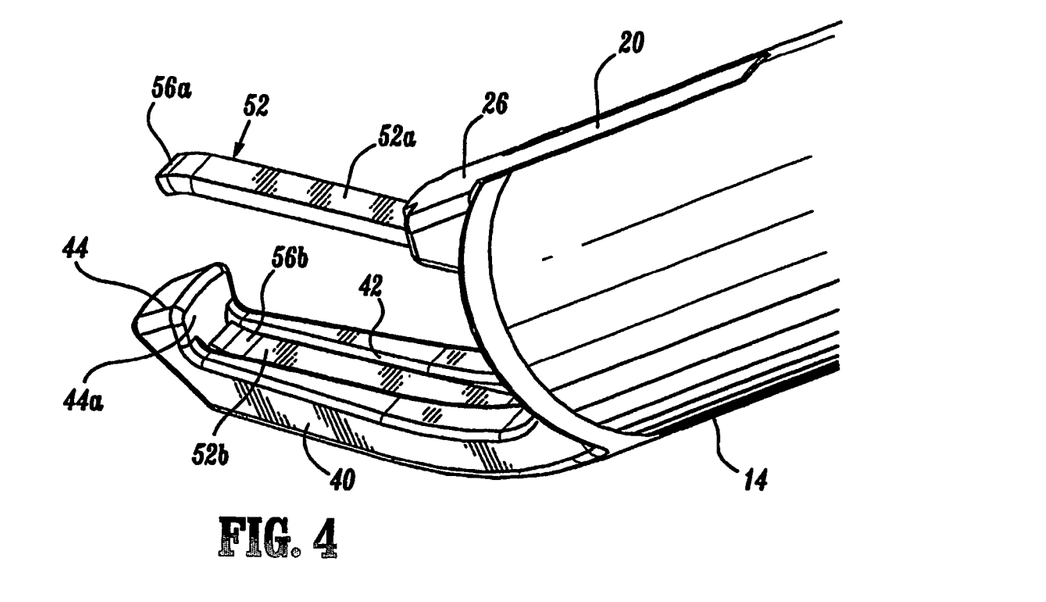
FIG. 4 is a side perspective view from the rear of the distal end of the clip applying apparatus shown in FIG. 1 with a clip positioned in the anvil jaw.
Figure 5:
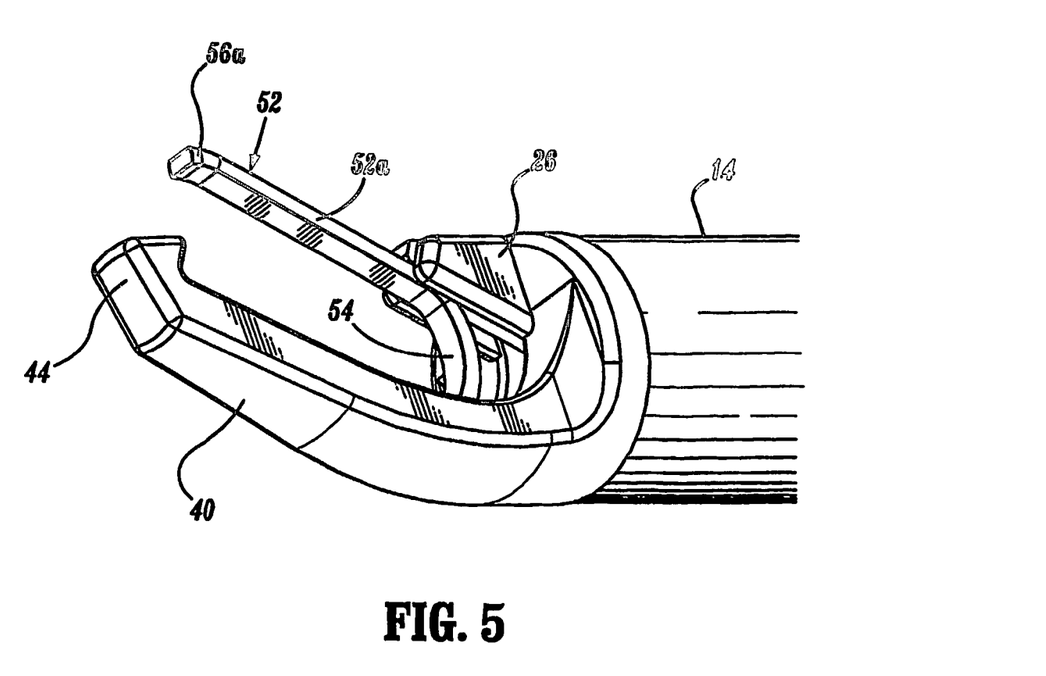
FIG. 5 is a bottom perspective view of the distal end of the clip applying apparatus shown in FIG. 1 with a clip positioned in the anvil jaw.
Figure 6:
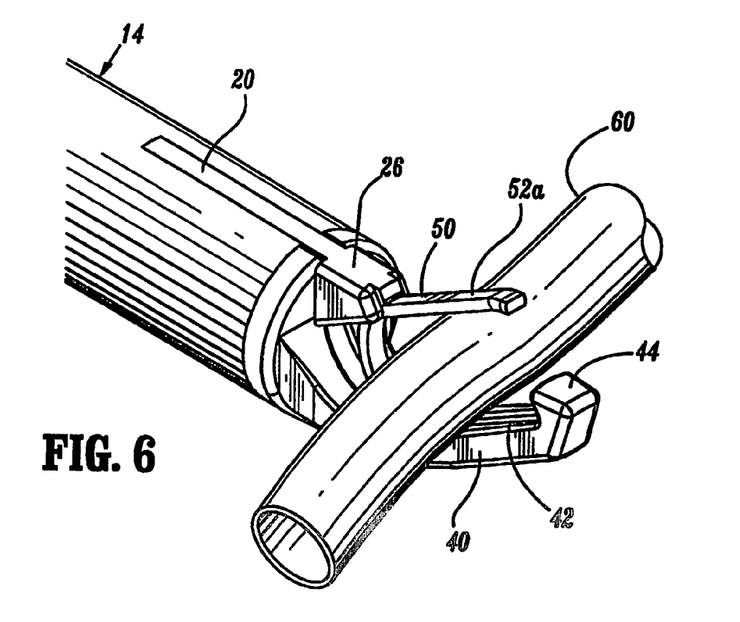
FIG. 6 is a side perspective view from the front of the distal end of the clip applying apparatus shown in FIG. 1 with an open clip positioned in the anvil jaw about a vessel and the crimping member or pusher in a retracted position.

Anvil 24 includes anvil body 38 and an anvil jaw 40. The longitudinal axis of anvil jaw 40 defines an angle θ with respect the longitudinal axis "X" of central body portion 14 (FIG. 3). By providing anvil 24 with an angled jaw, visibility of the surgical site is improved. In one embodiment, angle θ is between about 15 degrees and about 75 degrees. In another embodiment, angle θ is between about 20 degrees and about 45 degrees. In yet another embodiment, angle θ is between about 25 and about 30 degrees. In yet a further embodiment, angle θ is about 25 degrees. Although not necessary, angle θ may be substantially the same as angle β of angled crimping surface 22a. Angled jaw 40 defines a clip receiving channel 42 which is aligned with crimping member slot 32. Channel 42 is dimensioned to receive a leg 52b of clip 50 and channel 42a is dimensioned to slidably receive crimping member 20 upon distal movement thereof. Channel 42a is also dimensioned to receive a portion of a clip of a single clip feed instrument or multiple clips of a multi-clip feed instrument. A stop member 44 having a surface 44a (FIG. 4) is formed at a distal end of channel 42 and engages a distal end 56b of leg 52b of clip 50 during clip formation to prevent the clip 50 from being pushed from or out of anvil jaw 40. Stop 44 and surface 44a are shaped in the form of a hook to facilitate use of the jaw and hook for dissection and manipulation of tissue. Clip receiving channel 42 and channel 42a also prevent clip 50 from being derailed from or misaligned with channel 42 and from being pushed from anvil jaw 40. Anvil body 38 is secured within the distal end of central body 14 using known fastening techniques, e.g., friction fit, welding, fusing, peening, crimping, threads, pins, adhesives, etc. Channel 42a formed through body 38 is contiguous with channel 42 and facilitates movement of crimping member 20 from a retracted position to an advanced position.

One embodiment of clip 50 is shown in FIG. 3. Clip 50 includes a pair of legs 52a and 52b and a backspan 54. In one embodiment, backspan 54 is curved or semi-circular however, other geometric configurations are also envisioned. Each leg 52a and 52b, typically, is substantially parallel to the other leg and may include a curved tip 56a and 56b, respectively, which curves towards the other curved tip of clip legs 52a and 52b. Curved tips 56a and 56b, when used, allow the legs to smoothly transverse channel 42 and anvil jaw 40 without binding within the jaw during loading and deformation of the clip 50. In one embodiment, clip 50 is constructed from a surgical grade metal such as titanium. Alternately, other materials suitable for surgical use and having the requisite strength and deformation characteristics may be used to construct the clip 50, e.g., filled or unfilled polymeric or plastic, absorbable materials, etc.

Operation of clip applying instrument 10 will now be described in detail with reference to FIGS. 6-10. In use, a clip 50 is positioned in anvil jaw 40 with leg 52b of clip 50 supported in channel 42 of anvil jaw 40 and the proximal end of leg 52a located in channel 28 of head portion 26 of crimping member 20 (See FIGS. 3, 6 and 7). To prevent the clip 50 from becoming disengaged from anvil jaw 40 after it has been loaded, clip 50 may be shaped and/or dimensioned such that it must be elastically deformed slightly to position the clip 50 between anvil jaw 40 and head portion 26 of crimping member 20. As can be appreciated, this maintains the clip 50 under slight tension within the anvil jaw 40. This prevents slippage or unintentional dislodgement of the clip 50 prior to deformation.

Figure 7:
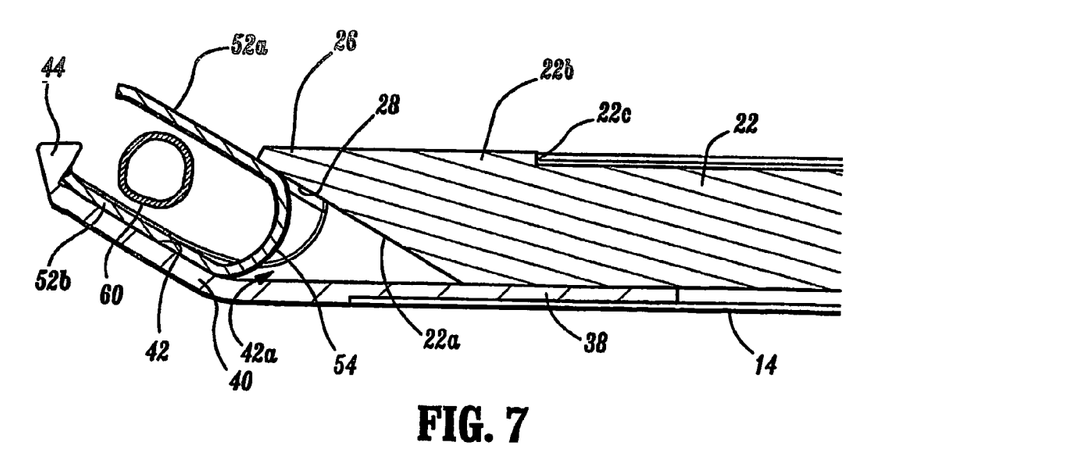
FIG. 7 is a side cross-sectional view of the distal end of the clip applying apparatus shown in FIG. 1 with an open clip positioned in the anvil jaw about a vessel and the crimping member or pusher in a retracted position.

With reference to FIG. 7, a properly loaded clip 50, prior to formation, has one leg 52b that lies along the anvil 24 in channel 42 and another leg 52a that extends distally from the channel 28 of crimping member 20 in a radially outward direction. Leg 52a extends radially outward from the longitudinal axis. The curved tip 56a of leg 52a is located radially outward beyond the anvil 24, the crimping member 20, and the body portion 14.

After a clip 50 has been loaded into anvil jaw 40, clip applying apparatus 10 can be manipulated to position jaw mechanism 16 adjacent a surgical site to position clip 50 about tissue 60 to be ligated. This may be accomplished by inserting central body portion 14 of apparatus 10 through an incision or a cannula or cannula assembly or via direct access to the surgical site.

Figure 8:
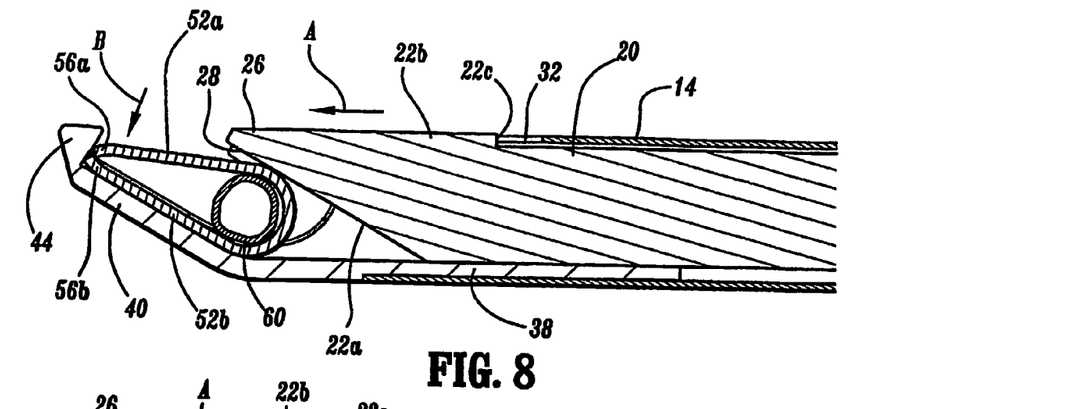
FIG. 8 is a side cross-sectional view of the distal end of the clip applying apparatus shown in FIG. 1 with a clip positioned in the anvil jaw about a vessel and the crimping member in a partially advanced position.

Referring to FIG. 8, when clip 50 is properly positioned about tissue, vessel 60, and pivotable trigger 12b are actuated, i.e., compressed towards stationary handle 12a (See FIG. 1), to advance crimping member 20 in the direction indicated by arrow "A" towards anvil jaw 40. During the initial stage of advancement of crimping member 20, because crimping surface 22a is angled, upper leg 52a bends downwardly towards lower leg 52b in the direction indicated by arrow "B" such that tips 56a and 56b are moved into engagement with each other prior to the proximal portion of legs 52a and 52b becoming engaged. By crimping clip 52 in this manner, tissue to be ligated is prevented from exiting or being totally or partially expelled from the confines of the clip during clip formation. It is also envisioned that the tips 56a and 56b may be configured to overlap or matingly engage to secure the clip 50 about the vessel 60.

Figure 10:
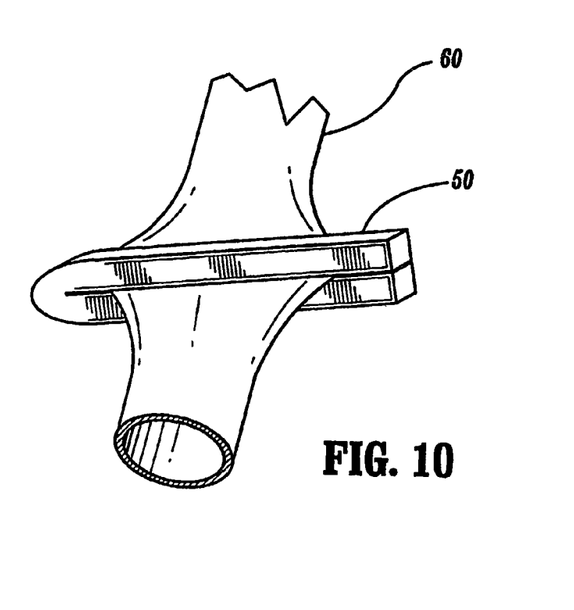
FIG. 10 is a perspective partial cross-sectional view of a clip of the clip applying apparatus shown in FIG. 1 crimped about a portion of a vessel.

Referring to FIGS. 9 and 10, crimping member 20 is moved to the fully advanced position (FIG. 9) in the direction indicated by arrow "A" to fully deform or crimp clip 52. Thereafter, pivotable handle 12b can be released to retract crimping member 20 and release clip 52 from anvil jaw 40. (See FIG. 10.)

The benefits of the presently disclosed clip applying apparatus 10 include improved visibility at the surgical site. This is due to the fact that one side of the anvil jaw 40 is angled outwardly from and unobstructed by the distal end of the clip applying apparatus 10. Further, by initiating clip closure at the tips 56a and 56b of the clip legs 52a and 52b, improved tissue confinement is achieved.

Although the illustrative embodiments of the present disclosure have been described herein with reference to the accompanying drawings, it is to be understood that this disclosure is not limited to those precise embodiments and that various other changes and modifications may be affected therein by one skilled in the art without departing from the scope or spirit of the disclosure. For example, although clip applying apparatus 10 has been disclosed as a single clip applicator, it is envisioned that with modifications, it can be employed for applying a series or multiplicity of clips, such as from a cartridge mounted within the instrument as disclosed in the U.S. patents identified above and incorporated herein by reference. All such changes and modifications are intended to be included within the scope of any appended claims.

What is claimed is:

1. A clip applying apparatus comprising:
    a handle assembly;
    a body portion extending distally from the handle assembly and defining a longitudinal axis, the body portion including a crimping member operably associated with the handle assembly, the crimping member being movable between a retracted position and an advanced position in response to actuation of the handle assembly;
    a jaw mechanism including a stationary jaw and a movable jaw, the movable jaw being supported on the crimping member, the stationary jaw including an anvil jaw that is linear along an entire length of the anvil jaw, the anvil jaw defining a longitudinal axis which forms an angle θ of between about 15 degrees and about 75 degrees with respect to the longitudinal axis of the body portion; and
    a clip having a pair of spaced apart legs interconnected by a backspan, the clip being supported on the stationary jaw,
    the movable jaw being movable between a proximal-most position, wherein the stationary jaw and the movable jaw are in an unapproximated position, and a distal-most position, wherein the stationary jaw and the movable jaw are in an approximated position such that the stationary jaw is in contact with the movable jaw and the movable jaw is in contact with the clip along an entire length of one of the pair of spaced legs of the clip to crimp the clip between the stationary jaw and the movable jaw, and
    wherein upon movement of the movable jaw from the proximal-most position to the distal-most position, the stationary and movable jaws first approximate a tip of each of the pair of spaced legs of the clip, and then approximate the backspan of the clip, one of the pair of spaced apart legs of the clip extending radially outward beyond the body portion and the jaw mechanism when the movable jaw is in the proximal-most position.

2. A clip applying apparatus according to claim 1, wherein the movable jaw is formed on a distal end of the crimping member.

3. A clip applying apparatus according to claim 2, wherein the movable jaw includes a distally located crimping surface positioned to engage the clip supported on the stationary jaw.

4. A clip applying apparatus according to claim 3, wherein the crimping surface defines an acute angle β with respect to the longitudinal axis of the body portion.

5. A clip applying apparatus according to claim 4, wherein angle β is substantially the same as angle θ.

6. A clip applying apparatus according to claim 3, wherein the movable jaw includes a head portion defining a recessed channel for receiving a portion of the clip supported on the stationary jaw.

7. A clip applying apparatus according to claim 1, wherein each of the pair of spaced legs includes a curved tip, each curved tip being curved inwardly towards the other of the pair of spaced legs.

8. A clip applying apparatus according to claim 1, wherein the stationary jaw includes a clip receiving channel configured to at least partially receive one of the pair of spaced legs, wherein when the one spaced leg is received in the clip receiving channel of the stationary jaw, a proximal end of the other spaced leg is received in a recessed channel defined within a head portion of the movable jaw.

9. A clip applying apparatus according to claim 8, wherein the crimping member is linearly movable along the longitudinal axis of the body portion such that upon movement of the crimping member from its retracted position towards its advanced position, the head portion deforms a distal end of the other spaced leg of the pair of spaced legs towards the one spaced leg to approximate the distal ends of the spaced legs of the clip prior to approximating the proximal ends of the spaced legs of the clip.

10. A clip applying apparatus according to claim 9, wherein a distal end of the stationary jaw includes a stop member positioned to engage the distal end of the one leg of the pair of spaced legs to prevent the clip from being pushed from the stationary jaw during actuation of the crimping member.

11. A clip applying apparatus according to claim 1, wherein the stationary jaw includes a clip receiving channel, and wherein a distal end of the clip receiving channel of the stationary jaw includes a stop member positioned to engage the tip of the leg of the clip supported on the stationary jaw, to thereby inhibit axial translation of the leg of the clip in the clip receiving channel of the stationary jaw, and wherein the movable jaw includes an open ended clip receiving channel.

12. A clip applying apparatus according to claim 11, wherein the stop member is hook-shaped to facilitate grasping of tissue.

13. A clip applying apparatus according to claim 1, wherein the body portion includes a distal end having an elongated slot and the crimping member includes a raised surface, the raised surface of the crimping member being slidably positioned in the elongated slot of the body portion.

14. A clip applying apparatus according to claim 13, wherein a proximal end of the raised surface defines a shoulder, the shoulder abutting the body portion at a position adjacent a proximal end of the elongated slot of the body portion to limit proximal movement of the crimping member.

15. A clip applying apparatus according to claim 1, wherein angle θ is between about 20 degrees and about 45 degrees.

16. A clip applying apparatus according to claim 15, wherein angle θ is about 25 degrees.

17. A clip applying apparatus comprising:
a handle assembly including a stationary handle and a pivotable trigger;
a body portion extending distally from the handle assembly and defining a longitudinal axis, the body portion including a crimping member operably associated with the handle assembly, the crimping member being movable between a retracted position, which is an initial position of the crimping member, and an advanced position, which is a final position of the crimping member, in response to actuation of the pivotable trigger;
a jaw mechanism including a stationary jaw and a movable jaw, the stationary jaw including an anvil jaw that is linear along an entire length of the anvil jaw, the anvil jaw defining a longitudinal axis which forms an angle θ of about 25 degrees with respect to the longitudinal axis of the body portion, the stationary jaw including a stop member located on a distal end thereof; and
a clip having a pair of spaced apart legs interconnected by a backspan, the clip being supported on the stationary jaw, wherein the stop member is positioned to contact the movable jaw and is positioned to engage the clip to prevent the clip from being pushed from the stationary jaw during actuation of the crimping member;
wherein the movable jaw is formed on a distal end of the crimping member and includes a distally located crimping surface positioned to engage an entire length of the leg of the clip supported on the stationary jaw, the crimping surface defining an angle β which is substantially the same as angle θ, the movable jaw having a head portion defining a recessed channel for receiving a first leg of the clip supported on the stationary jaw,
wherein a second leg of the clip extends radially outward beyond both the body portion and the jaw mechanism when the crimping member is disposed in the retracted position, wherein the body portion includes a distal end having an elongated slot and the crimping member includes a raised surface having a proximal end defining a shoulder, the raised surface of the crimping member being slidably positioned in the elongated slot of the body portion such that the shoulder abuts the body portion at a position adjacent a proximal end of the elongated slot to limit proximal movement of the crimping member, and
wherein upon movement of the movable jaw from a proximal-most position to a distal-most position, the stationary and movable jaws first approximate a tip of each of the pair of spaced legs of the clip, and then approximate a backspan of the clip.

18. A clip applying apparatus according to claim 1, wherein the movable jaw is configured to move linearly along the longitudinal axis, from a point proximal to the stationary jaw towards the stationary jaw.

19. A clip applying apparatus according to claim 17, wherein the movable jaw is configured to move linearly along the longitudinal axis, from a point proximal to the stationary jaw towards the stationary jaw.

20. A clip applying apparatus comprising:
a handle assembly;
a body portion extending distally from the handle assembly and defining a longitudinal axis, the body portion including a crimping member operably associated with the handle assembly, the crimping member being movable along a longitudinal axis between a retracted proximal position and an advanced distal position in response to actuation of the handle assembly; and
a jaw mechanism including a stationary jaw and a movable jaw, wherein when the crimping member is in the retracted position the movable jaw is completely unapproximated from the stationary jaw; and
a clip being supported on the stationary jaw, the clip having a pair of spaced legs interconnected by a backspan,
the movable jaw being formed on a distal end of the crimping member and including a distally located crimping surface positioned to engage an entire length of a leg of the clip supported on the stationary jaw, the movable jaw being movable into contact with the stationary jaw to crimp the clip between the stationary jaw and the movable jaw, the movable jaw positioned to first approximate a tip of each of the pair of spaced legs of the clip, and then approximate the backspan of the clip,
wherein the stationary jaw includes a clip receiving channel, and wherein a distal end of the clip receiving channel of the stationary jaw includes a stop member positioned to engage a tip of the leg of the clip supported on the stationary jaw, to thereby inhibit axial translation of the leg of the clip in the clip receiving channel of the stationary jaw, and
wherein the movable jaw includes an open ended clip receiving channel, the clip receiving channel of the stationary jaw and the open ended clip receiving channel of the movable jaw defining an open end, and wherein one of the legs of the clip extends radially outward beyond the open end when the crimping member is in the retracted position.

* * * * *